| United States Patent [19] | [11] Patent Number: 4,933,377 |
| --- | --- |
| Saeva et al. | [45] Date of Patent: Jun. 12, 1990 |

[54] NOVEL SULFONIUM SALTS AND THE USE THEREOF AS PHOTOINITIATORS

[76] Inventors: Franklin D. Saeva; David T. Breslin, both c/o Eastman Kodak Company, Rochester, N.Y. 14650

[21] Appl. No.: 161,811

[22] Filed: Feb. 29, 1988

[51] Int. Cl.$^5$ .................... C08G 59/68; C08G 59/72
[52] U.S. Cl. ........................ 522/31; 430/280; 430/914; 430/922; 522/170; 544/347; 556/64; 556/69; 562/45; 562/113; 558/411; 558/413; 558/396; 558/397; 568/54; 568/56
[58] Field of Search .................... 522/31, 170

[56] References Cited

U.S. PATENT DOCUMENTS

| | | | |
| --- | --- | --- | --- |
| 4,058,400 | 11/1977 | Crivello | 96/86 |
| 4,058,401 | 11/1977 | Crivello | 96/115 R |
| 4,069,054 | 1/1978 | Smith | 96/115 P |
| 4,120,866 | 10/1978 | Winkler | 260/315 |
| 4,138,255 | 2/1979 | Crivello | 96/35.1 |
| 4,250,053 | 2/1981 | Smith | 252/426 |
| 4,291,114 | 9/1981 | Berggren et al. | 430/253 |
| 4,760,013 | 7/1988 | Hacker | 430/280 |
| 4,837,124 | 6/1989 | Wu et al. | 522/31 |

FOREIGN PATENT DOCUMENTS 1526923 10/1975 United Kingdom .

OTHER PUBLICATIONS

"Advanced Organic Chemistry", Second Ed., 1977, J. March, McGraw-Hill Co., pp. 20, 21 & 22.

*Primary Examiner*—John C. Bleutge
*Assistant Examiner*—Arthur H. Koeckert

[57] ABSTRACT

Sulfonium and oxysulfonium salts, useful as photoinitiators, have directly attached to the sulfur atom thereof:

at least one aromatic or heterocyclic aromatic substituent containing at least 14 aromatic atoms and having a removable positive hydrogen ion, said substituent exhibiting a higher energy occupied molecular orbital than at least one other substituent directly attached to said sulfur atom;

and at least one substituent comprising an electron withdrawing group and exhibiting a lower energy unoccupied molecular orbital than at least one other substituent directly attached to said sulfur atom;

said salt being capable, upon exposure to visible radiation, of undergoing irreversible intramolecular rearrangement to form a Bronsted acid comprising the anion of said salt and said removable positive hydrogen ion.

5 Claims, No Drawings

NOVEL SULFONIUM SALTS AND THE USE THEREOF AS PHOTOINITIATORS

This invention relates to novel sulfonium salts and more particularly to light sensitive sulfonium salts. It also relates to the use of such salts as photoinitiators.

It is well known that sulfonium salts can be used as photoinitiators which produce acid to cure a wide variety of materials. See, for example, UV Curing: Science and Technology, edited by S. Peter Pappas and published (1978) by Technology Marketing Corporation, 64 Westover Road, Stamford, Conn. 06902, pages 58–71. However, as noted therein on page 67, triaryl sulfonium salts do not absorb light in the visible region of the spectrum, and are commonly used in combination with photosensitizers in order to carry out visible light-induced photoinitiation.

Crivello in U.S. Pat. No. 4,058,400 (1977) discloses a series of sulfonium compounds which produce an acid when exposed to UV radiation (see column 6, lines 22–44). Although Crivello suggests that the sulfonium salts may contain an anthryl radical (column 2, line 50) there is no recognition or teaching of specific sulfonium salts which, upon exposure to visible radiation, would irreversibly decompose to release a Bronsted acid. Generally similar disclosures appear in Crivello U.S. Pat. No. 4,058,401 (1977), Smith U.S. Pat. No. 4,069,054 (1978), Crivello U.S. Pat. No. 4,138,255 (1979), Smith U.S. Pat. No. 4,250,053 (1981), Berggren U.S. Pat. No. 4,291,114 (1981); and Allen U.S. Pat. No. 4,373,040 (1983).

Crivello in U.S. Pat. 4,259,454 (1981) discloses heat curable compositions comprising a dialkylhydroxyarylsulfonium salt, a cationically polymerizable organic material and an organic oxidant initiator. There is no recognition or teaching by Crivello that any of the sulfonium salts disclosed therein would absorb visible radiation. Further, these hydroxyarylsulfonium salts would not, because of the presence of the hydroxy group on the aryl ring, release a positive hydrogen ion from the aryl ring to form a Bronsted acid. The hydroxyarylsulfonium salts of Crivello do not irreversibly decompose, as is desirable for efficient release of a Bronsted acid.

Winkler in U.S. Pat. No. 4,120,866 (1978) discloses a preparation for arylsulfonium salts in which an aromatic compound is reacted with a sulfoxide, e.g., dimethyl sulfoxide, in the presence of hydrogen fluoride Winkler suggests anthracene as one possible starting material; however, the sulfoxide starting materials suggested by Winkler would not result in sulfonium salts which have a substituent comprising an electron withdrawing group attached to the sulfur atom on the sulfonium salt. The Winkler anthyryl sulfonium salts (as noted above) are not irreversibly decomposed upon exposure to radiation, and are not suitable for the efficient generation of a Bronsted acid.

There is a need in the art for aromatic sulfonium salts which, upon exposure to visible radiation, irreversibly decompose to form a Bronsted acid comprised of the anion of the aromatic sulfonium salt and a positive hydrogen ion from the aryl ring of the sulfonium salt.

The compounds of this invention are sulfonium and oxysulfonium salts having directly attached to the sulfur atom thereof:
at least one aromatic or heterocyclic aromatic substituent containing at least 14 aromatic atoms and having a removable positive hydrogen ion, said substituent exhibiting a higher energy occupied molecular orbital than at least one other substituent directly attached to said sulfur atom;
and at least one substituent comprising an electron withdrawing group and exhibiting a lower energy unoccupied molecular orbital than at least one other substituent directly attached to said sulfur atom;
said salts being capable, upon exposure to visible radiation, of undergoing irreversible intramolecular rearrangement to form a Bronsted acid comprising the anion of said salt and said removable positive hydrogen ion.

The sulfonium salts of this invention absorb visible radiation. This property was unexpected because anthracene itself is not visible light absorbing. Further, generic suggestions of anthyrylsulfonium salts in the literature suggest that they would absorb in the UV, but not the visible, region of the spectrum.

The subject sulfonium salts do not need a second component (e.g., water or an alcohol) to provide a Bronsted acid; rather, the proton of the Bronsted acid is released from the aromatic ring subsequent to intramolecular photocleavage and radical recombination. Corresponding phosphonium and ammonium salts are incapable of intramolecular rearrangement, and require an additional compound, such as water or alcohol. The corresponding arsonium salts are not sufficiently reactive to function as efficient photoinitiators.

The sulfonium salts of this invention are particularly advantageous because they photobleach when irradiated. The photoproducts of the sulfonium salts absorb at a shorter wavelength than the starting materials. This allows the sulfonium salts of the invention to be used in thicker coatings (e.g., over 5 micron) than commercially available sulfonium salt sensitizers, which do not bleach when irradiated. It also permits the use of the subject photoinitiators to prepare shaped objects.

A particularly preferred class of sulfonium photoinitiators is represented by the following formula

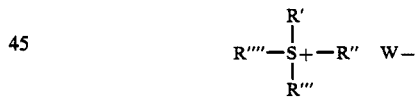

wherein:
R' represents an electron donating aromatic or heterocyclic aromatic substituent having at least 14 atoms the aromatic ring and having a removable positive hydrogen ion bonded to one of the aromatic atoms. The aromatic group preferably contains 14–20 carbon atoms, and most preferably is anthryl. Heterocyclic aromatic groups preferably contain from 14 to 20 atoms, from 1 to 4 of which are hetero atoms, such as N; a highly preferred heterocyclic group is a 1-phenazine group. The aromatic or heterocyclic aromatic substituent advantageously is electron donating, and accordingly may be substituted with such groups as alkyl, amide, sulfonamide, etc.;

R'' represents the same substituent as R' or R''', or an optionally substituted phenyl group, naphthyl group or alkyl group having from 1 to 18 carbon atoms;

R''' represents an electron withdrawing alkyl, aryl or heterocyclic group, such as alkyl groups having from 1 to 18, and most preferably 1 to 4 carbon atoms; aryl groups having from 6 to 10 carbon atoms, and most preferably a phenyl group; and heterocyclic groups having from 1 to 4 rings and containing from 1 to 3 hetero atoms, such as N, S, O, Se or Te. The R''' substituent preferably contains an electron withdrawing group, such as halogen (preferably Cl or Br); CN, $NO_2$, $-SO_2-$ and the like;

R'''' represents an electron pair or oxygen; and

W- represents an anion capable of forming a Bronsted acid preferably having a pKa of less than 7. Preferred anions include $BF_4^-$, $ClO_4^-$, $AsF_6^-$, $PF_6^-$, $CH_3SO_3^-$, $CF_3SO_3^-$, $FeCl_4^-$, $BiCl_4^{-2}$, $SnCl_6^-$, $AlF_6^{-3}$, $GaCl_4$, $InF_4^-$, $TiF_6$, $ZrF_6^-$, $SbF_6^-$, and p-toluenesulfonate.

The subject compounds are capable, upon exposure to visible radiation, of undergoing irreversible intramolecular rearrangement to form a Bronsted acid comprising W- and the removable positive hydrogen ion of R'.

Typical specific useful sulfonium photoiniators are listed below:

1. (9-Anthryl)methyl-p-cyanobenzyl sulfonium hexafluorophosphate
2. 9-(10-Methoxyanthryl)methyl-p-cyanobenzyl sulfonium hexafluoroantimonate
3. (9-Anthryl)methyl-2,3,4,5,6,-pentafluorobenzyl sulfonium trifluoromethanesulfonate
4. 9-(10-Methylanthryl)methyl-p-cyanobenzyl sulfonium hexafluorophosphate.
5. (5-Naphthacenyl)methyl-cyanomethyl sulfonium trifluoromethanesulfonate
6. (5-Naphthacenyl)methyl-fluoromethyl sulfonium hexafluoroantimonate
7. 9-(10-Chloroanthryl)methyl-p-fluorobenzyl sulfonium p-toluenesulfonate
8. (9-Anthryl)ethyl-p-cyanobenzyl sulfonium tetrafluoroborate
9. (9-Anthryl)methyl-2,4-dicyanobenzyl sulfonium hexafluorophosphate
10. 9-(10-Methoxyanthryl)ethyl-2,3,4,5,6,-pentafluorobenzyl sulfonium perchlorate.

The photoinitiators of this invention can be used in any application where it is desirable to release a Bronsted acid. The subject photoinitiators are especially useful in compositions which are curable by a Bronsted acid. Such compositions, also called cationically curable compounds, include cyclic formals and acetals, vinyl ethers, cyclic ethers, lactones, polysiloxanes, urea-formaldehyde resins, melamine-formaldehyde resins, and epoxides. A more comprehensive list is detailed in *Cationic Polymerisation of Olefins: A Critical Inventory* J. P. Kennedy, Wiley Interscience Pub. 1975. Epoxy resins are particularly preferred.

The useful epoxy resins preferably contain a plurality of epoxy groups and may be based on the reaction product of Bisphenol A (i.e. 2,2-bis(4-hydroxyphenyl)propane) and epichlorohydrin, e.g. the resins sold under the registered Trade Mark Araldite by Ciba-Geigy Ltd., or are the reaction product of epichlorohydrin with a phenol-formaldehyde resin of relatively low molecular weight, e.g. epoxy-Novolaks (available, for example from Dow), or other modified epoxy resins as disclosed in *UV Curing: Science and Technology* (cited above). Still other useful epoxy resins and ether-containing materials which are polymerizable to a higher molecular weight are listed in Berggren et al U.S. Pat. No. 4,291,114 (1981) col. 4 line 37 through col. 6 line 23 and the silicone curable compositions disclosed by Eckberg U.S. Pat. No. 4,547,431 (1985) col. 3 line 29 through col. 4 line 17.

The photoinitiators of the invention can comprise from 0.1 to 30, and preferable from 5 to 25 percent by weight of the curable composition.

The photoinitiators of the invention can be used to provide protective coatings by imagewise or non-imagewise polymerization of monomers, e.g., the epoxide or ether containing monomers referred to above. The present photoinitiators can be used advantageously to provide overcoats for optical recording elements, such as those described by Thomas et al U.S. Pat. No. 4,380,769 issued Apr. 19, 1983. Such recording elements have on a support, in order, a smoothing layer, a reflection layer, a heat-deformable optical recording layer and a protective overcoat layer.

The photoinitiators of the invention can also be used in photoelectrographic elements which have a conductive layer in contact with an acid generating layer which contains a photoinitiator of the invention (the acid generating layer being free of photopolymerizable monomer), as described in Molaire et al U.S. patent application Ser. No. 856,543 filed April 28, 1986. Such elements can be imagewise exposed, the acid photogenerating layer can be electrostatically charged, and the resultant electrostatic image can be developed with charged toning particles. Also, the photoinitiators of the invention can be used in the electrophotographic elements and process described in Scozzofava et al U.S. Pat. No. 4,485,161 issued Nov. 27, 1984.

The photoinitiators of the invention can also be used in the method of making color filter arrays which is described by Molaire et al U.S. patent application Ser. No. 871,748 filed June 9, 1986. In that method, an electrophotographic element having a conductive layer in electrical contact with an acid photogenerating layer comprising an electrically insulating binder and being free of photopolymerizable materials, is imagewise exposed and electrostatically charged to form a latent image, and the latent image is developed with colored toner particles to form a single color array. Those steps can be repeated, with different colored toners to produce a multicolored filter array.

The following examples are included for a further understanding of the invention.

The compounds of this invention can be prepared by reacting a halo-substituted aromatic or heterocyclic compound with a suitable sulfide, e.g., an alkyl disulfide, to obtain a thio-substituted aromatic or heterocyclic intermediate which can be reacted with a suitable electron-withdrawing halide to provide the photoinitiators of the invention.

SYNTHESIS

9-Thiomethylanthracene

A solution of 15.0 g (58 mmoles) of 9-bromoanthracene in 75 mL of anhydrous THF (tetrahydrofuran) was cooled to −63 C., and 25 mL of 2.6 M n-butyl lithium (63 mmoles) was added over 45 min. The mixture was stirred for 30 min, and a solution of methyl disulfide 5.50 g, (63 mmoles) in 15 mL of dry THF was added over 30 min. The mixture was then quenched with 100 mL of 10% HCl. The acidic aqueous -THF layer was extracted with diethyl ether. The ether fractions were combined, washed with 10% NaOH, with $H_2O$, dried over $MgSO_4$, and flash evaporated to yield 12.50 g of dark yellow crystals. Recrystallization from cyclohexane yielded pale yellow crystals m.p. 63°–64.5° C. MS - m/e=224, H NMR 2.40 (s, 3H) arom 9.1–7.2 (m, 9H).

p-Cyanobenzylmethyl-9-anthrylsulfonium Trifluoromethanesulfonate

Silver trifluoromethanesulfonate 2.29 g (8.9 mmoles) was added to a solution of 2.0 g (8.9 mmol) 9-thiomethylanthracene, 1.75 g (8.9 mmoles) p-cyanobenzylbromide, and 30 mL of methylene chloride. The insoluble silver salts were filtered off after 3 hours, and the volume was reduced. The product solution was dropped into diethyl ether. The product precipitated from solution and the ether was decanted leaving the product as a yellow gum. Recrystallization from acetonitrile/ether yielded 0.28 g of light yellow crystals, m.p. 139°–40° C. MS(FD) m/e=340, NMR CD CN 3.70(s,3H) 5.48 (q, 2H) arom 9.1–7.27 (m, 14H).

Examples 1-3 illustrate the use of the photoinitiators of the invention in imagewise conductive polymer films for electrophotographic copying, circuit board fabrication, and fabrication of color filter arrays.

EXAMPLE 1

Electrophotographic Copying without Re-Exposure (9-Anthryl)methyl-p-cyanobenzylsulfonium trifluoromethanesulfonate (I) (10% by weight) was dissolved in sufficient dichloromethane along with polystyrene host polymer (90% by weight) to form a homogeneous solution. A film of the above composition was cast onto an aluminum substrate by spin coating to provide a film of about 5 microns in thickness. The solvent was allowed to evaporate from the film in a vacuum oven with heating (25°–50° C.). The polymer film was then exposed to visible light from a mercury-xenon light source in an imagewise fashion through a mask. The film was then charged with a corona while the conductor was held to ground. The ion charge discharged more rapidly in the irradiated regions due to the presence of the Bronsted acid released from (I) than in the non-irradiated areas, which produced a latent charged image which was developed by toning with a positively charged colored toner material. The toned image was transferred to paper and fused to form a permanent image. Additional copies of the charged image were made by repeating the toning and transfer process without repeating the exposure step. Generally similar results can be obtained when the sulfonium salt and polymer are used in weight percentages of from 1–20% sulfonium salt and 80–99% polymer; when the polymer is polyvinyl alcohol or polymethylmethacrylate and the conductive surface is indium tin oxide or tin oxide.

EXAMPLE 2

Circuit Board Fabrication (9-Anthryl)methyl-p-cyanobenzylsulfonium trifluoromethanesulfonate (I) (10% by weight) was dissolved in sufficient dichloromethane along with a polystyrene as a host polymer (90% by weight) to form a homogeneous solution. A film of the above composition was spin coated onto an aluminized polyester support to form a film about 5 microns in thickness. The solvent was allowed to evaporate from the film in a vacuum oven with heating (25°–50° C.). The polymer film was then exposed to visible light from a mercury-xenon source in an imagewise fashion through a mask. The film was then charged with a negative corona while the conductor was held to ground. The ion charge discharged more rapidly in the irradiated regions than in the non-irradiated areas producing a latent charged image. The latent charged image was then toned with a positive polymeric toner material. The imagewise toner image was then transferred to a sheet of metallic copper on an insulating substrate. The copper film not covered by the toner material was selectively removed by dissolving in nitric acid, in the presence of molecular oxygen to produce a copper pattern for a printed circuit board.

EXAMPLE 3

Fabrication of Color Filter Arrays (9-Anthryl)methyl-p-cyanobenzylsulfonium trifluoromethanesulfonate (I) (10% by weight) was dissolved in sufficient dichloromethane along with polymethylmethacrylate as host polymer (90% by weight) to form a homogeneous solution. A film of the above composition was spin coated onto a conductive tin oxide substrate to provide a film of 5 microns in thickness. The solvent was allowed to evaporate from the film in a vacuum oven with heating (25°–50° C.). The polymer film was then exposed to visible light from a mercury-xenon light source in an imagewise fashion through a mask. The film was then charged with a negative corona while the conductor was held to ground. The ion charge discharged more rapidly in the irradiated regions than in the non-irradiated areas producing a latent charged image which was developed by conventional toning with a positively charged blue toner. The blue toner image was transferred to a transparent receiver sheet. Yellow and red toner were transferred to the substrate in a similar fashion to obtain a high resolution three color filter array.

Examples 4 and 5 show the use of photoinitiators of the invention in imagewise dye bleaching processes for visible image formation and optical disc preformatting.

EXAMPLE 4

Imagewise Dye Absorption Changes

9-Anthryl)methyl-p-cyanobenzylsulfonium trifluoromethanesulfonate (I) (10% by weight) and propyl red indicator (5% by weight) were dissolved in sufficient dichloromethane along with polystyrene as the host polymer (85% by weight) to form a homogeneous solution. A film of the above composition was cast onto an aluminum substrate with a doctor blade to provide a film of about 1 micron in thickness. The solvent was allowed to evaporate from the film in a vacuum oven with heating (25°–50° C.). The polymer film was then exposed to visible light from a mercury-xenon light source in an imagewise fashion through a mask. The polymer film was transformed to a red color in the irradiated areas while the non-irradiated areas remain yellow in color.

EXAMPLE 5

Optical Disc Preformatting (Imagewise Dye Bleaching)

(9-Anthryl)methyl-p-cyanobenzylsulfonium trifluoromethanesulfonate (I) (10% by weight) and an infrared absorbing dye 2,3-diphenyl-7-(2-(9-julolidinyl)ethenyl)-1-oxo-1H-indolizinium trifluoromethanesulfonate (II) (5% by weight) that bleaches in the presence of acid was dissolved in sufficient dichloromethane along with polyvinylphenol as host polymer (85% by weight). A film of the above composition was cast onto aluminized polyester film by spin coating to provide a film 5 micron in thickness. The solvent was allowed to evaporate from the film in a vacuum oven with heating (25°–50° C.). The polymer film was then exposed to visible light from a laser light source in an imagewise fashion through laser scanning. In the irradiated areas a Bronsted acid was produced which transformed the infrared absorbing dye (II) to a colorless species to preformat the optical disc.

The following example shows the use of the photoinitiators of the invention in imagewise formation of silicon containing materials for photoresist applications using dry development.

EXAMPLE 6

Imagewise Formation of Silicon Containing Polymers (9-Anthryl)methyl-p-cyanobenzylsulfonium trifluoromethanesulfonate (I) (10% by weight) was dissolved in sufficient dichloromethane along with polyvinylphenol as host to form a homogeneous solution. A film of the above solution was cast on a silicon wafer. Irradiation of the film in an imagewise fashion with a mercury lamp produced a Bronsted acid. In the presence of trimethylsilylpropylene oxide vapors a silane polymer was deposited only in the irradiated areas of the above film. The film containing the deposited silane polymer was then subjected to an oxygen plasma to remove the material from the non-irradiated areas. This process can be used for the fabrication of microelectronic and electronic components and the like by dry processing.

Examples 7 and 8 show the use of the photoinitiators of the invention to produce the imagewise release of chemical fragments in a polymer system for photoresist applications.

EXAMPLE 7

Imagewise Release of a Chemical Fragment (9-Anthryl)methyl-p-cyanobenzylsulfonium trifluoromethanesulfonate (I) (10% by weight) was dissolved in sufficient dichloromethane solvent along with polyvinyl (4-t-butylphenylcarbonate) as host polymer (90% by weight) to make a homogeneous solution. A film of the polymer-photoacid composition was cast onto a silicon wafer. The film was then irradiated in an imagewise fashion with visible light from a mercury lamp. In the irradiated areas a Bronsted acid was produced which catalyzed the thermal transformation of the original polymer to polyvinylphenol. The regions containing the polyvinylphenol were then selectively removed with an aqueous base solution (10–50% hydroxide solution).

EXAMPLE 8

Imagewise Release of a Silane Chemical Fragment (9-Anthryl)methyl-p-cyanobenzylsulfonium trifluoromethanesulfonate (I) (10% by weight) was dissolved in sufficient dichloromethane along with a polymer containing pendant allyl-t-butyldimethyl silyl groups (90% by weight) to make a homogeneous solution. A film of the polymer-photoacid composition was cast onto a silicon wafer. The film was then irradiated in an imagewise fashion using a mercury-xenon lamp. In the irradiated areas a Bronsted acid was produced which catalyzed the thermal transformation to the vinyl polymer without the pendant silane functionality. Exposure of the irradiated and heated film to an oxygen plasma selectively removed the irradiated areas by a completely dry process.

Example 9 shows the use of the photoinitiators of the invention to photopolymerize an epoxide protective coating.

EXAMPLE 9

Protective Coatings by Photopolymerization (9-Anthryl)methyl-p-cyanobenzylsulfonium trifluoromethanesulfonate (I) (10% by weight) was dissolved in sufficient dichloromethane along with cyclohexene oxide (30% by weight) in a low molecular weight hydroxylated prepolymer (60% by weight). A film of the prepolymer-photoacid composition was cast onto an optical disc as substrate. The film was then irradiated in non-imagewise fashion with visible light from a mercury-xenon lamp. In the irradiated areas a Bronsted acid was produced which catalyzed the polymerization of the epoxide species to form a high molecular weight polymer protective coating.

Unlike commercially available sulfonium salt sensitizers, the sulfonium salt photoinitiators of this invention bleach when irradiated. This property allows the use of the photoinitiators of the invention in thick films (e.g., over 5 micron thick) or in applications in which 'shaped' articles are found. This is illustrated in Example 10.

EXAMPLE 10

Photopolymerization of Thick Films and Articles

Example 9 is repeated except that the film of prepolymer-photoacid is about 15 microns in thickness. Because the decomposition products of the sulfonium salt photoinitiator are bleached, and do not absorb significant radiation over 400 nm, the initiator functions throughout the thickness of the film to release a Bronsted acid and effects polymerization. Similarly, shaped articles can be formed by holding the prepolymeric-initiator composition in a suitable mold, irradiating the composition to release Bronsted acid and effect curing of the prepolymer. Example 11 shows the use of the photoinitiators of the invention to produce an imagewise color shift.

EXAMPLE 11

Color Shift by Release of Bronsted Acid

Two samples of an ethyl cellulose polymer film containing 1% by weight of (9-anthryl)methyl-p-cyanobenzylsulfonium trifluoromethanesulfonate (I) and 0.05% by weight of propyl red was irradiated through a Corning 3-74 filter (which cuts off radiation below 400 nm) for 5 and 30 minutes with a mercury-xenon lamp positioned 18 inches from the lamp. A water filter 4 inches in thickness was placed between the lamp and the sample to eliminate the absorption of infrared radiation. In both samples, the visible light irradiation resulted in the release of a Bronsted acid from the sulfonium salt (1); the Bronsted acid protonated the propyl red, to shift the absorption to longer wavelength providing a color change from yellow to red.

Results generally similar to those of Examples 1-11 can be achieved when other photoinitiators of the invention are substituted for the (9-anthryl)methyl-p-cyanobenzylsulfonium trifluoromethanesulfonate (I) used therein. However, when other anthrylium sulfonium salts, such as hydroxy substrated anthrylium salts are substituted for (I), unsatisfactory results are obtained because such sulfonium salts are not irreversible photo-decomposed. When still other structurally related sulfonium salts which do not contain a substituent having an electron withdrawing group, and which substituent does not exhibit a lower energy unoccupied molecular orbital than at least one other substituent directly attached to the sulfur atom of the sulfonium salt, unsatisfactory results are obtained because such sulfonium salts do not irreversibly decompose when irradiated to form a Bronsted acid.

The invention has been described in detail with particular reference to preferred embodiments thereof, but it will be understood that variations and modifications can be effected within the spirit and scope of the invention.

What is claimed is:

1. A composition of matter comprising a material curable by a Bronsted acid, and a sulfonium or oxysulfonium salt having directly attached to the sulfur atom thereof:
   at least one aromatic or heterocyclic aromatic substituent containing at least 14 aromatic atoms and having a removable positive hydrogen ion, said substituent exhibiting a higher energy occupied molecular orbital than at least one other substituent directly attached to said sulfur atom;
   and at least one substituent comprising an electron withdrawing group and exhibiting a lower energy unoccupied molecular orbital than at least one other substituent directly attached to said sulfur atom;
   said salts being capable, upon exposure to visible radiation, of undergoing irreversible intramolecular rearrangement to form a Bronsted acid comprising the anion of said salt and said removable positive hydrogen ion.

2. A composition of matter comprising a material curable by a Bronsted acid, and a compound having the formula:

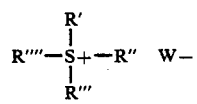

wherein:
   R' represents an electron donating aromatic or heterocyclic aromatic substituent having at least 14 atoms in the aromatic ring and having a removable positive hydrogen ion bonded to one of the aromatic atoms;
   R" represents the same substituent as R' or R''', or an optionally substituted phenyl group, naphthyl group or alkyl group having from 1 to 18 carbon atoms;
   R''' represents an electron withdrawing alkyl, aryl or heterocyclic group;
   R'''' represents an electron pair or oxygen;
   W- represents an anion capable of forming a Bronsted acid having a pKa of less than 7;
   said compound being capable, upon exposure to visible radiation, of undergoing irreversible intramolecular rearrangement to form a Bronsted acid comprising W- and said removable positive hydrogen ion of R'.

3. A photocurable composition comprising an epoxy resin polymerizable to a higher molecular weight, and a sulfonium or oxysulfonium salt having directly attached to the sulfur atom thereof:
   at least one aromatic or heterocyclic aromatic substituent containing at least 14 aromatic atoms and having a removable positive hydrogen ion, said substituent exhibiting a higher energy occupied molecular orbital than at least one other substituent directly attached to said sulfur atom;
   and at least one substituent comprising an electron withdrawing group and exhibiting a lower energy unoccupied molecular orbital than at least one other substituent directly attached to said sulfur atom;
   said salts being capable, upon exposure to visible radiation, of undergoing irreversible intramolecular rearrangement to form a Bronsted acid comprising the anion of said salt and said removable positive hydrogen ion.

4. A photocurable composition comprising an epoxy resin polymerisable to a higher molecular weight, and a compound having the formula:

wherein:
   R' represent an electron donating aromatic or heterocyclic aromatic substituent having at least 14 atoms in the aromatic ring and having a removable positive hydrogen ion bonded to one of the aromatic atoms;
   R" represents the same substituent as R' or R''', or an optionally substituted phenyl group, naphthyl group or alkyl group having from 1 to 18 carbon atoms;
   R''' represents an electron withdrawing alkyl, aryl or heterocyclic group;
   R'''' represents an electron pair or oxygen;
   W- represents an anion capable of forming a Bronsted acid having a pKa of less than 7;
   said compound being capable, upon exposure to visible radiation, of undergoing irreversible intramolecular rearrangement to form a Bronsted acid comprising W- and said removable positive hydrogen ion of R'.

5. A composition of matter comprising a material curable by a bronsted acid and, as photoinitiator, (9-Anthryl)methyl-p-cyanobenzylsulfonium triflurome-thanesulfonate.

* * * * *